US005693531A

United States Patent [19]
Chiorini et al.

[11] Patent Number: 5,693,531
[45] Date of Patent: Dec. 2, 1997

[54] VECTOR SYSTEMS FOR THE GENERATION OF ADENO-ASSOCIATED VIRUS PARTICLES

[75] Inventors: John A. Chiorini, Silver Spring; Robert Kotin, Rockville; Brian Safer, Silver Spring; Elena Urcelay, Bethesda, all of Md.

[73] Assignee: The United States of America as represented by the Department of Health and Human Services, Washington, D.C.

[21] Appl. No.: 157,740

[22] Filed: Nov. 24, 1993

[51] Int. Cl.$^6$ .......................... C12N 15/64; C12N 15/85; C12N 15/86; C12N 15/09
[52] U.S. Cl. .................. 435/325; 435/320.1; 435/172.3; 424/93.1
[58] Field of Search .......................... 435/172.3, 235.1, 435/240.2, 320.1, 325; 424/93.1

[56] References Cited

U.S. PATENT DOCUMENTS

| | | | |
|---|---|---|---|
| 4,797,368 | 1/1989 | Carter et al. | 435/320.1 |
| 5,139,941 | 8/1992 | Muzyczka et al. | 435/172.3 |
| 5,173,411 | 12/1992 | Lebkowski et al. | 435/6 |
| 5,252,479 | 10/1993 | Srivastava | 435/235.1 |
| 5,436,146 | 7/1995 | Shenk et al. | 435/172.3 |
| 5,474,935 | 12/1995 | Chatterjee et al. | 435/320.1 |
| 5,478,745 | 12/1995 | Samulski et al. | 435/320.1 |

OTHER PUBLICATIONS

Milligan (1993) "The basic science of gene therapy" Science 260:926–931.
Carter, *Current Opinion in Biotechnology*, vol. 3, pp. 533–539 (1992).
Hermonat, et al., *Pro. Nat. Acad. Sci. USA*, vol. 81, pp. 6466–6470 (Oct. 1984).
Gerard, et al., *Mol. Cell. Biol.*, vol. 5, No. 11, pp. 3231–3240 (Nov. 1985).
Sedivy, et al., *Cell*, vol. 50, pp. 379–389 (Jul. 31, 1987).
Samulski, et al., *J. Virol.*, vol. 63, No. 9, pp. 3822–3828 (Sep. 1989).
Kelly, *The Harvey Lecture*, Series 85, pp. 172–188 (1991).
Engelhardt, et al., *Nature Genetics*, vol. 4, pp. 27–34 (May 1993).

*Primary Examiner*—Jasemine C. Chambers
*Assistant Examiner*—Scott D. Priebe
*Attorney, Agent, or Firm*—Elliot M. Olstein; Raymond J. Lillie

[57] ABSTRACT

A vector system comprising a first vector, which is an adeno-associated viral vector, and which includes an adeno-associated virus 5'ITR, an adeno-associated virus 3'ITR, and at least one heterologous DNA sequence. The vector system also includes a second vector which includes an inducible origin of replication, such as an SV40 origin of replication, which is capable of being induced or activated by an agent, such as the SV40 T-antigen. The second vector also includes DNA sequences encoding the adeno-associated virus rep and cap proteins. When induced by an agent, the second vector may replicate to a high copy number, and thereby increased numbers of infectious adeno-associated viral particles may be generated.

6 Claims, 9 Drawing Sheets

VECTOR SYSTEMS FOR THE GENERATION OF ADENO-ASSOCIATED VIRUS PARTICLES

This invention relates to adeno-associated virus vectors and to adeno-associated virus particles generated therefrom. More particularly, this invention relates to a vector system which generates high copy numbers of the structural genes of adeno-associated virus.

Production of recombinant adeno-associated virus (or AAV) requires the presence of the adeno-associated virus ITR's in cis, and the adeno-associated virus rep and cap gene products in trans. In present adeno-associated virus vector systems, the rep and cap genes are not provided in a replication competent plasmid and, therefore, there is no increase in copy number over the genes which are placed into the packaging cell via transfection.

It is therefore an object of the present invention to provide an adeno-associated virus vector system capable of generating an increased copy number of the structural adeno-associated virus rep and cap genes.

In accordance with an aspect of the present invention, there is provided a vector system comprising a first vector and a second vector. The first vector is an adeno-associated viral vector. The first vector includes an adeno-associated virus 5'ITR; at least one heterologous DNA sequence; and an adeno-associated virus 3'ITR.

The second vector includes an inducible origin of replication selected from the group consisting of an SV40 origin of replication, a polyoma origin of replication, a bacteriophage origin of replication (such as, for example, a bacteriophage T7 origin of replication), a yeast origin of replication, and other high copy origins of replication, which is capable of being activated by an agent. The second vector also includes a DNA sequence encoding the adeno-associated virus rep protein, and a DNA sequence encoding the adeno-associated virus cap protein. In one alternative, the DNA sequences encoding the AAV rep and cap proteins may be contained in separate vectors.

In one embodiment, the inducible origin of replication is the SV40 origin of replication, and the agent is the SV40 T-antigen, which activates the SV40 origin of replication in order to generate a high copy number of the second vector and the AAV rep and cap genes contained therein. Although the scope of the present invention is not to be limited to any theoretical reasoning, the SV40 T-antigen binds to the SV40 origin of replication, which is followed by local unwinding of the SV40 origin of replication. Following the unwinding of the SV40 origin of replication, there is priming and initiation of DNA synthesis, followed by elongation of nascent chains. Such interaction between the SV40 T-antigen and the SV40 origin of replication is described further in Kelly, "DNA Replication in Mammalian Cells: Insights from the SV40 Model System," in *The Harvey Lectures*, Series 85, pgs. 173–188, Wiley-Liss, Inc. (1991). The SV40 T-antigen may be supplied by administering the SV40 T-antigen to cells transduced with the vector system, or the SV40 T-antigen may be supplied from a constitutively expressing cell line, such as COS cells, or by an inducible expression system.

Thus, in one embodiment, the vector system further comprises a third vector including a DNA sequence encoding the agent, such as but not limited to the SV40 T-antigen hereinabove described, and an inducible promoter controlling the DNA sequence encoding the agent.

In one alternative, the DNA encoding the SV40 T-antigen may be a temperature-sensitive mutated DNA, such as that described in Sedivy, et al., Cell, Vol. 50, pgs. 379–389 (Jul. 31, 1987).

Inducible promoters which may be employed include, but are not limited to, the metallothionein promoter, the tetracycline promoter, the dioxin-inducible promoter, and the IPTG-inducible promoter.

In one embodiment, the inducible promoter is a metallothionein promoter.

In a preferred embodiment, the vector system includes a first vector which is an adeno-associated viral vector including the 5'ITR, the 3'ITR, and at least one heterologous DNA sequence. The vector system also includes a second vector which includes an SV40 origin of replication, and the AAV rep and cap genes. The AAV rep and cap genes are under the control of a suitable promoter, such as, for example, the adeno-associated virus P5, P19, or P40 promoters; the HIV-LTR promoter; and the SV40 promoter. A third vector includes a DNA sequence encoding the SV40 T-antigen under the control of the mouse metallothionein promoter. The mouse metallothionein promoter is induced in the presence of metals such as copper, cadmium, and zinc, as well as by hormones and interferons. In the presence of an inducing metal, the gene encoding the SV40 T-antigen, when expressed, binds to the SV40 origin of replication of the second vector, whereby the second vector, which includes the AAV rep and cap genes, can replicate to a high copy number. The term "high copy number" as used herein, means from about $10^2$ to about $10^5$ copies per cell, preferably from about $10^3$ to about $10^4$ copies per cell, and more preferably about $10^4$ copies per cell. The replication of the second vector to a high copy number enables the generation of an increased number of viral particles from the vector system upon transfection of the vector system into a packaging cell line.

In a most preferred embodiment, the second vector is constructed by inserting the SV40 origin of replication into the EcoRV site of pBluescriptKS$^+$, and the BalI A-fragment of adeno-associated virus is inserted into the SmaI site of pBluescriptKS$^+$. Cleavage of adeno-associated virus with BalI removes the terminal 121 nucleotides from both ends of the adeno-associated virus genome. The resulting construct (i.e., the second vector) contains the AAV rep and cap genes, but is replication defective via the AAV 5'ITR and 3'ITR, which are absent from the vector. Such vector can replicate, however via the SV40 origin of replication in the presence of SV40 T-antigen.

The third vector, which includes a metallothionein promoter and a DNA sequence encoding the SV40 T-antigen, is co-transfected with the second vector into a packaging cell line, such as, for example, the BSC-1 cell line, the CMT-3 cell line, the 293 cell line, and Vero cells. Upon addition of a metal, such as cadmium and zinc, to the packaging cells, the third vector will express the SV40 T-antigen, which will bind to the SV40 origin of replication of the second vector. When the SV40 T-antigen binds to the SV40 origin of replication, the second vector replicates to a high copy number (i.e., up to about $10^4$ copies per cell.). At from about 24 hours to about 48 hours after transfection of the packaging cells with the second vector and the third vector, the packaging cells are transfected with the first vector, which includes the adeno-associated virus 5'ITR and 3'ITR and at least one heterologous DNA sequence, and with an adenovirus. The adenovirus early gene products induce the adeno-associated virus promoters of the second vector, whereby the first vector replicates, as well as induce the adeno-associated virus promoters of the second vector, and infectious adeno-associated virus particles are generated from the first and second vectors. Such infectious viral particles include the at least one heterologous DNA sequence. The infectious viral particles may be used to transduce eukaryotic cells, which may be employed in a gene therapy procedure.

DNA sequences encoding therapeutic agents which may be placed into the first vector include, but are not limited to, DNA sequences encoding tumor necrosis factor (TNF) genes, such as TNF-α; genes encoding interferons such as Interferon-α, Interferon-β, and Interferon-Γ; genes encoding interleukins such as IL-1, Il-1β, and Interleukins 2 through 14; genes encoding GM-CSF; genes encoding adenosine deaminase, or ADA; genes which encode cellular growth factors, such as lymphokines, which are growth factors for lymphocytes; genes encoding soluble CD4, Factor VIII, Factor IX, T-cell receptors, the LDL receptor, ApoE, ApoC, the alpha-1 antitrypsin (α-1AT) gene, the ornithine transcarbamylase (OTC) gene, the CFTR gene, the insulin gene, Fc receptors for antigen-binding domains of antibodies, and antisense sequences which inhibit viral replication, such as antisense sequences which inhibit replication of hepatitis B or hepatitis non-A non-B virus.

The DNA sequence encoding at least one therapeutic agent is under the control of a suitable promoter. Suitable promoters which may be employed include, but are not limited to adeno-associated virus promoters; adenoviral promoters, such as the adenoviral major late promoter; or hetorologous promoters, such as the cytomegalovirus (CMV) promoter; the respiratory syncytial virus promoter; the Rous Sarcoma Virus (RSV) promoter; inducible promoters, such as the MMTV promoter, the metallothionein promoter; and heat shock promoters. It is to be understood, however, that the scope of the present invention is not to be limited to specific foreign genes or promoters.

Eukaryotic cells which may be transduced with the infectious viral particles include, but are not limited to, primary cells, such as primary nucleated blood cells, such as leukocytes, granulocytes, monocytes, macrophages, lymphocytes (including T-lymphocytes and B-lmphocytes), totipotent stem cells, and tumor infiltrating lymphocytes (TIL cells); bone marrow cells; endothelial cells; epithelial cells; keratinocytes; stem cells; hepatocytes, including hepatocyte precursor cells; hepatocytes, including hepatocyte precursor cells; fibroblasts; mesenchymal cells; mesothelial cells; and parenchymal cells.

In one embodiment, the cells may be targeted to a specific site, whereby the cells function as a therapeutic at such site. Alternatively, the cells may be cells which are not targeted to a specific site, and such cells function as a systemic therapeutic.

The cells may be administered in combination with a pharmaceutically acceptable carrier suitable for administration to a patient. The carrier may be a liquid carrier (for example, a saline solution), or a solid carrier such as, for example, an implant or microcarrier beads. In employing a liquid carrier, the cells may be introduced intravenously, subcutaneously, intramuscularly, intraperitoneally, intralesionally, etc. In yet another embodiment, the cells may be administered by transplanting or grafting the cells.

Transduced cells may be used, for example, in the treatment of cancer in a human by transducing into human primary cells, such as, for example, blood cells, which specifically "target" to a tumor and which have been removed from a cancer patient and expanded in culture, infectious viral particles in accordance with the present invention which contain genes that enhance the anti-tumor effects of the blood cells. The blood cells can be expanded in number before or after transduction with the infectious viral particles containing the desired genes. Thus, the procedure is performed in such a manner that upon injection into the patient, the transformed blood cells will produce the agent in the patient's body, preferably at the site of the tumor itself.

The gene carried by the blood cells can be any gene which directly or indirectly enhances the therapeutic effects of the blood cells. The gene carried by the blood cells can be any gene which allows the blood cells to exert a therapeutic effect that it would not ordinarily have, such as a gene encoding a clotting factor useful in the treatment of hemophilia. The gene can encode one or more products having therapeutic effects. Examples of suitable genes include those that encode cytokines such as TNF, interleukins (interleukins 1–14), interferons (α, β, γ-interferons), T-cell receptor proteins and Fc receptors for antigen-binding domains of antibodies, such as immunoglobulins.

Additional examples of suitable genes include genes that modify primary cells such as blood cells to "target" to a site in the body to which the blood cells would not ordinarily "target," thereby making possible the use of the blood cell's therapeutic properties at that site. In this fashion, blood cells such as TIL cells can be modified, for example, by introducing a Fab portion of a monoclonal antibody into the cells, thereby enabling the cells to recognize a chosen antigen. Likewise, blood cells having therapeutic properties can be used to target, for example, a tumor, that the blood cells would not normally target to. Other genes useful in cancer therapy can be used to encode chemotactic factors which cause an inflammatory response at a specific site, thereby having a therapeutic effect. Other examples of suitable genes include genes encoding soluble CD4 which is used in the treatment of AIDS and genes encoding α-antitrypsin, which is useful in the treatment of emphysema caused by α-antitrypsin deficiency.

The transduced cells of the present invention are useful in the treatment of a variety of diseases including but not limited to adenosine deaminase deficiency, sickle cell anemia, thalassemia, hemophilia, diabetes, α-antitrypsin deficiency, brain disorders such as Alzheimer's disease, phenylketonuria and other illnesses such as growth disorders and heart diseases, for example, those caused by alterations in the way cholesterol is metabolized and defects of the immune system.

The transduced cells may be used for the delivery of polypeptides or proteins which are useful in prevention and therapy of an acquired or an inherited defect in hepatocyte (liver) function. For example, they can be used to correct an inherited deficiency of the low density lipoprotein (LDL) receptor, and/or to correct an inherited deficiency of ornithine transcarbamylase (OTC), which results in congenital hyperammonemia.

For example, hepatocyte precursors transduced with infectious viral particles of the present invention may be grown in tissue culture vessels; removed from the culture vessel; and introduced into the body. This can be done surgically, for example. In this case, the tissue which is made up of transduced hepatocyte precursors capable of expressing the nucleotide sequence of interest is grafted or transplanted into the body. For example, it can be placed in the abdominal cavity in contact with/grafted onto the liver or in close proximity to the liver. Alternatively, the transduced hepatocyte precursors can be attached to a support, such as, for example, microcarrier beads, which are introduced (e.g., by injection) into the peritoneal space of the recipient. Direct injection of the transduced hepatocyte precursors into the liver or other sites is also contemplated. Alternatively, the transduced hepatocyte precursors may be injected into the portal venous system or may be injected intrasplenically. Subsequent to the injection of such cells into the spleen, the cells may be transported by the circulatory system to the liver. Once in the liver, such cells may express the gene(s) of interest and/or differentiate into mature hepatocytes which express the gene(s) of interest.

The transduced cells of the present invention may be employed to treat acquired infectious diseases, such as diseases resulting from viral infection. For example, transduced hepatocyte precursors may be employed to treat viral hepatitis, particularly hepatitis B or non-A non-B hepatitis. For example, an infectious viral particle containing a gene encoding an antisense gene could be transduced into hepatocyte precursors to inhibit viral replication. In this case, the infectious viral particle, which includes a vector including a structural hepatitis gene in the reverse or opposite orientation, would be introduced into hepatocyte precursors, resulting in production in the transduced hepatocyte precursors and any mature hepatocytes differentiated therefrom of an antisense gene capable of inactivating the hepatitis virus or its RNA transcripts. Alternatively, the hepatocyte precursors may be transduced with an infectious viral particle including a vector which includes a gene which encodes a protein, such as, for example, α-interferon, which may confer resistance to the hepatitis virus.

The invention will now be described with respect to the drawings, wherein.

The invention will now be described with respect to the following examples; it is to be understood, however, that the scope of the present invention is not to be limited thereby.

EXAMPLE

A. Construction of AAVrnLac

Figure 1:
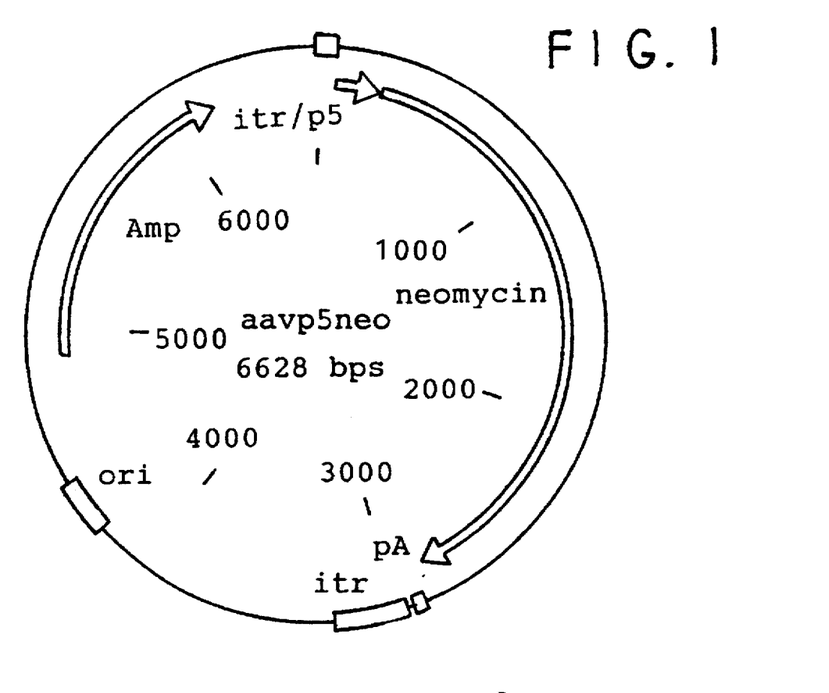
FIG. 1 is a map of plasmid AAVp5neo.
Figure 2:
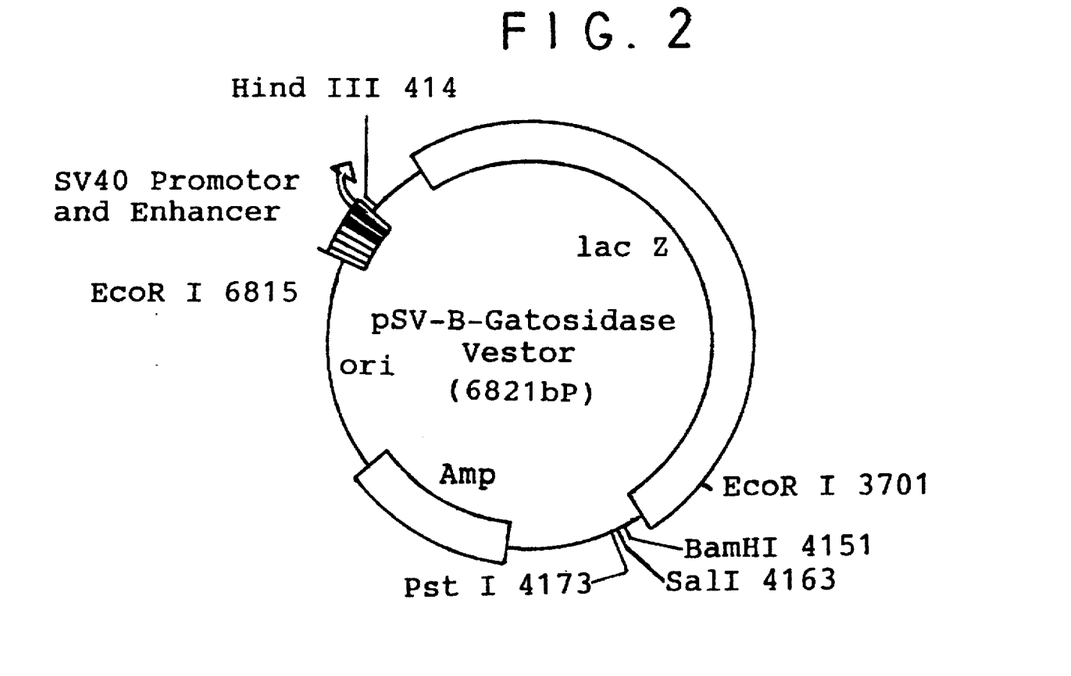
FIG. 2 is a map of plasmid pSV-β-Galactosidase.
Figure 3:
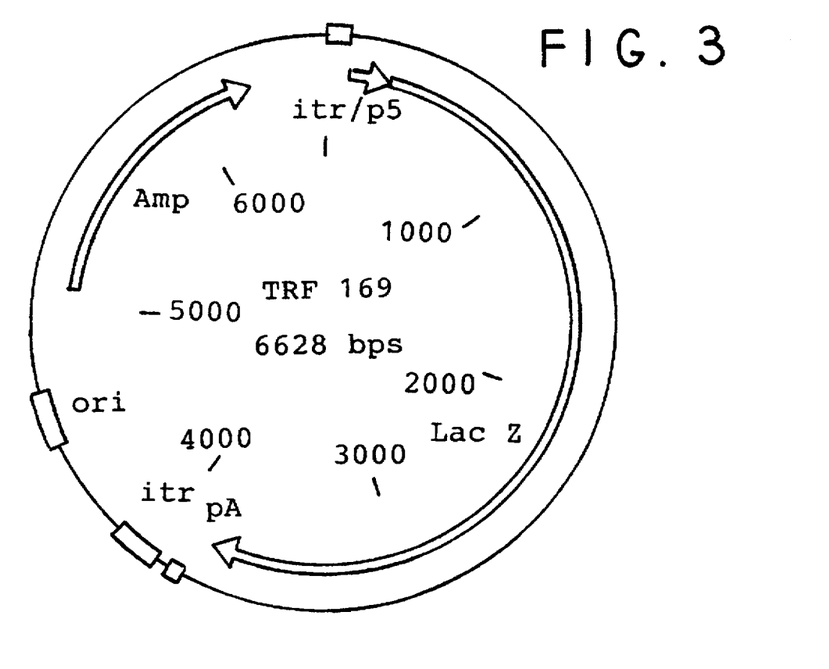
FIG. 3 is a map of plasmid TRF169.

Plasmid AAVp5neo (Flotte, et al., *Am. J. Respir. Cell Mol. Biol.*, Vol. 7, pgs. 349–356 (1992)) (FIG. 1) was cut with HindIII and KpnI to remove the neo$^R$ gene, and the KpnI/BamHI fragment from pSV-βgalactosidase (Promega) (FIG. 2) was blunted and cloned into the blunted sites of the plasmid to form plasmid TRF169. (FIG. 3).

Figure 4:
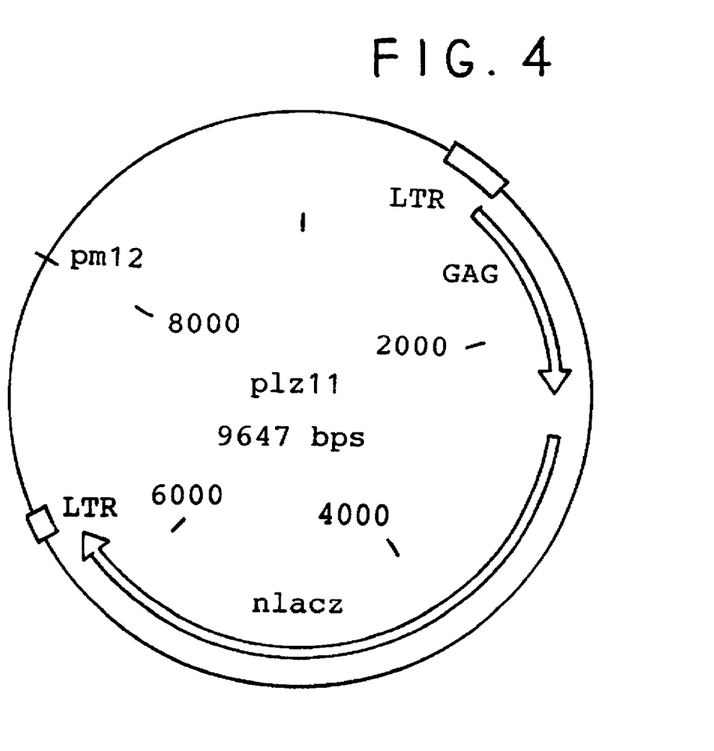
FIG. 4 is a map of plasmid LZ11.
Figure 5:
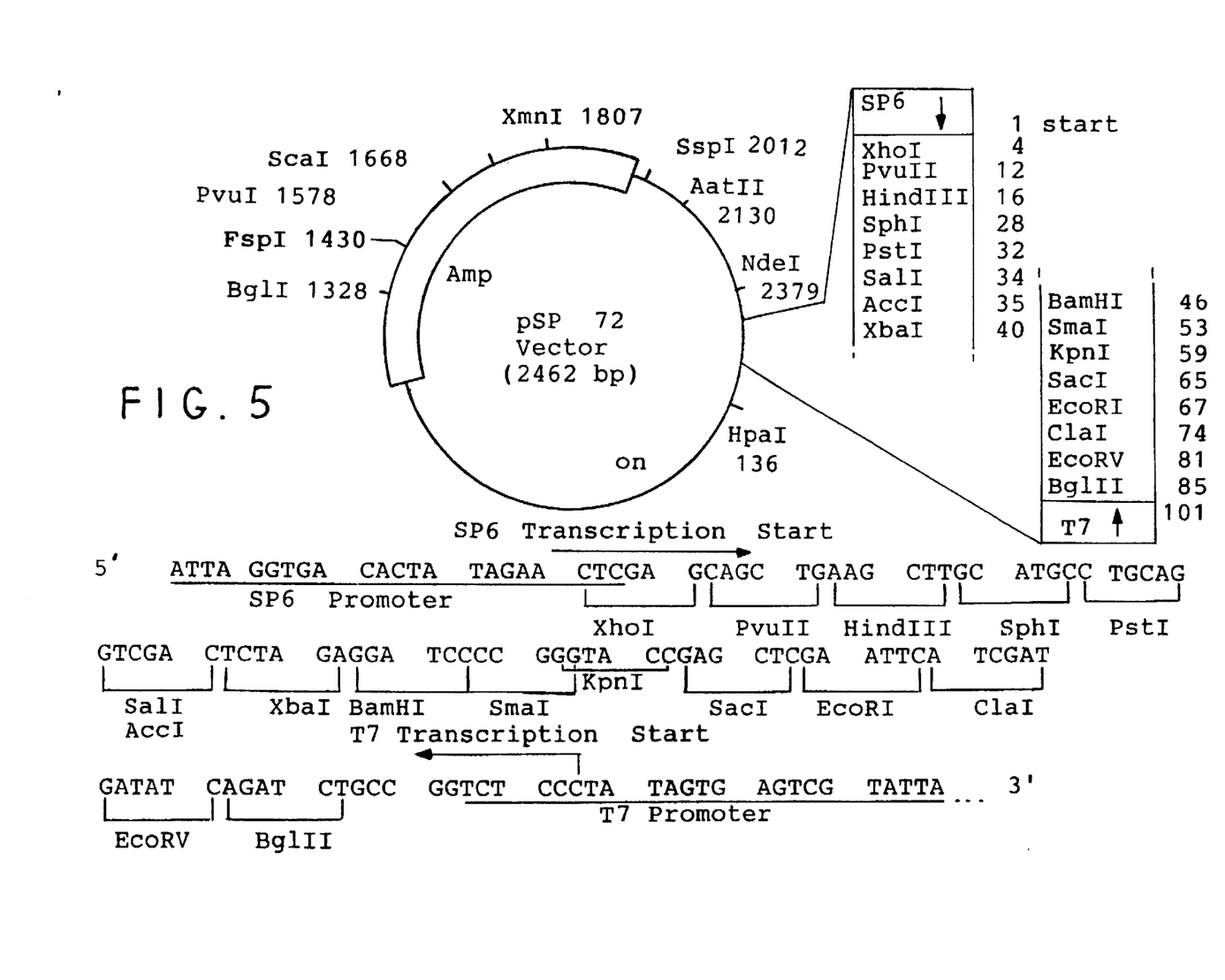
FIG. 5 is a map of plasmid pSP72.
Figure 6:
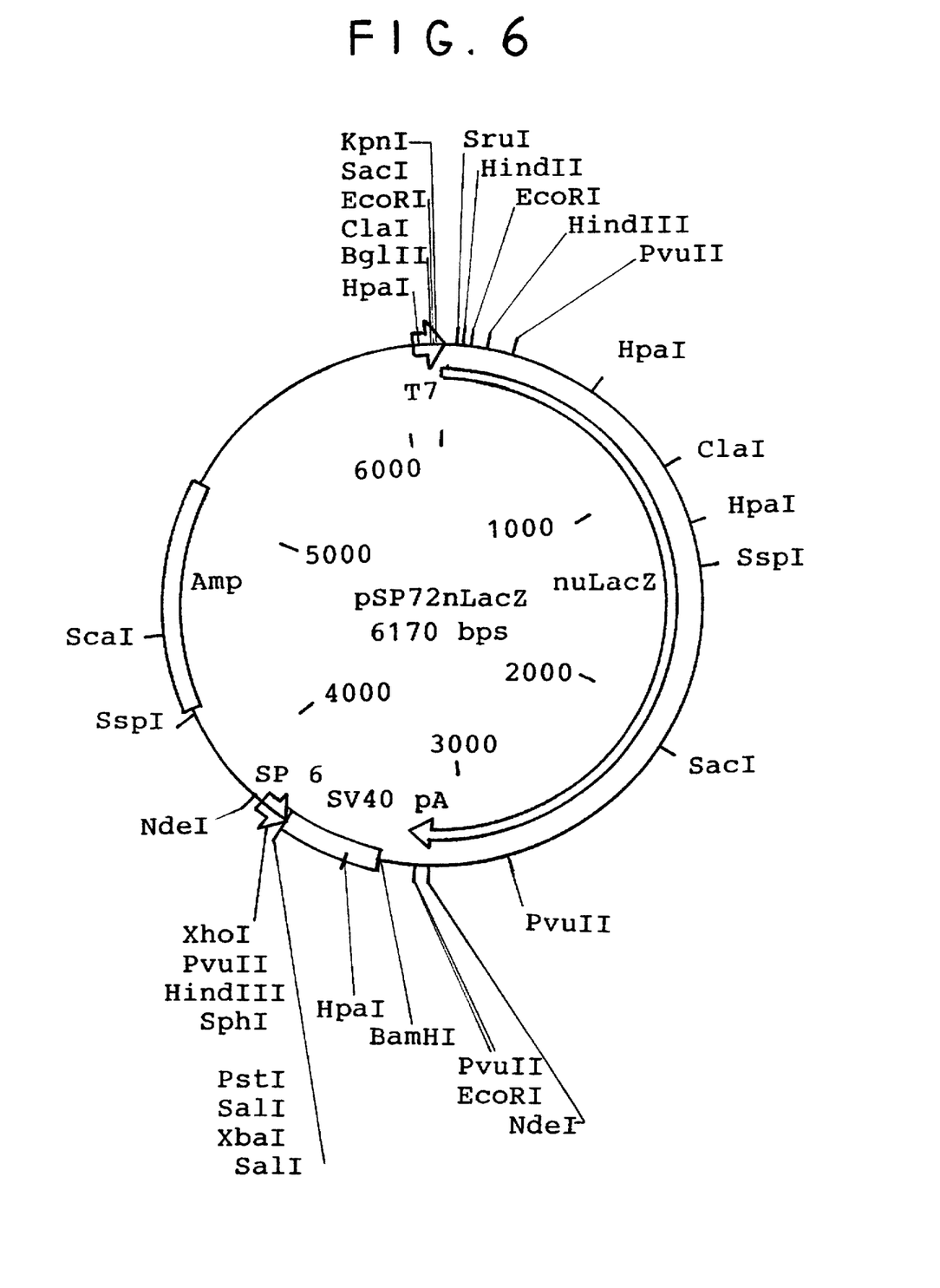
FIG. 6 is a map of plasmid pSP72nLacZ (SEQ ID NO: 1)
Figure 7:
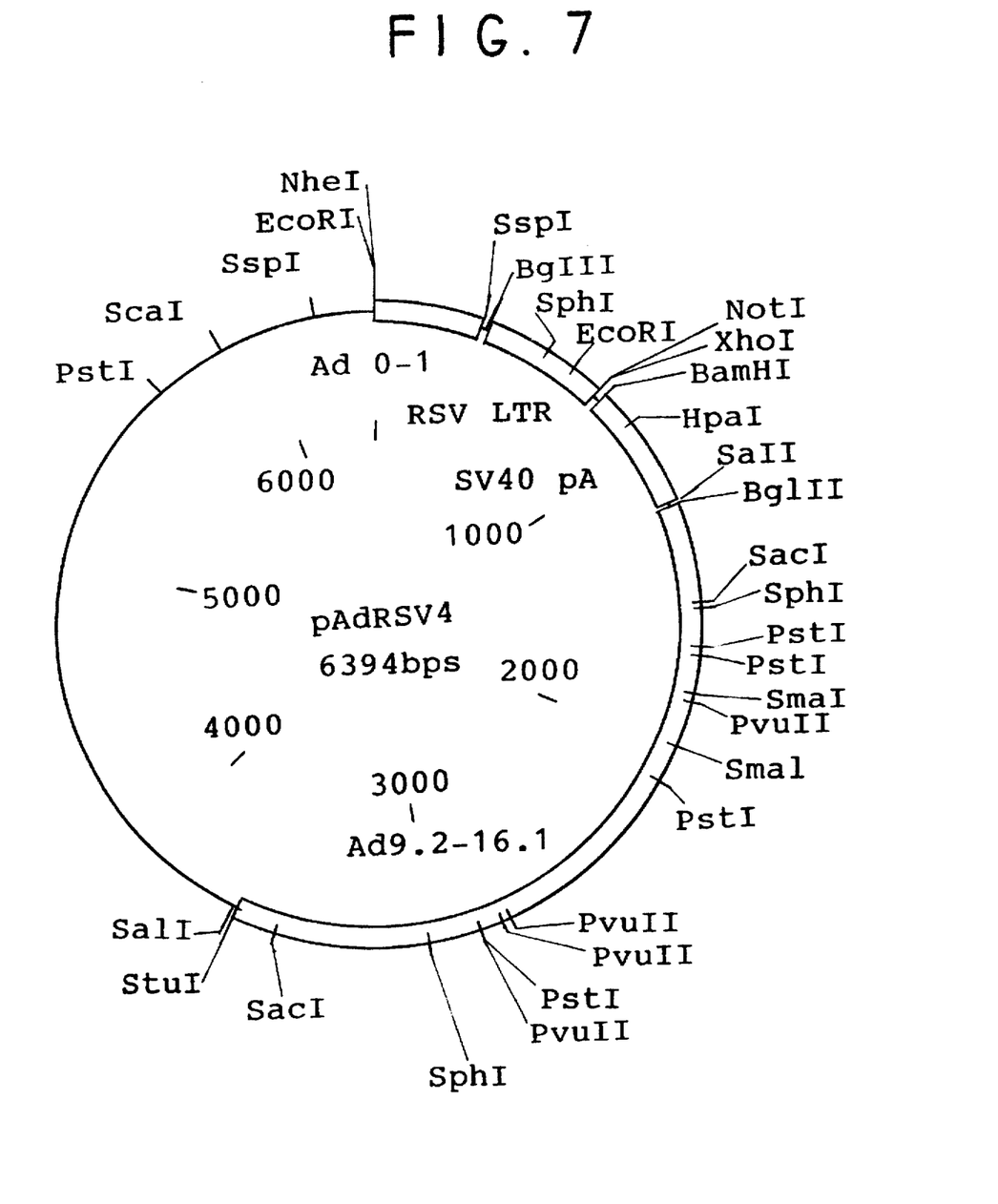
FIG. 7 is a map of plasmid pAdRSV4.
Figure 8:
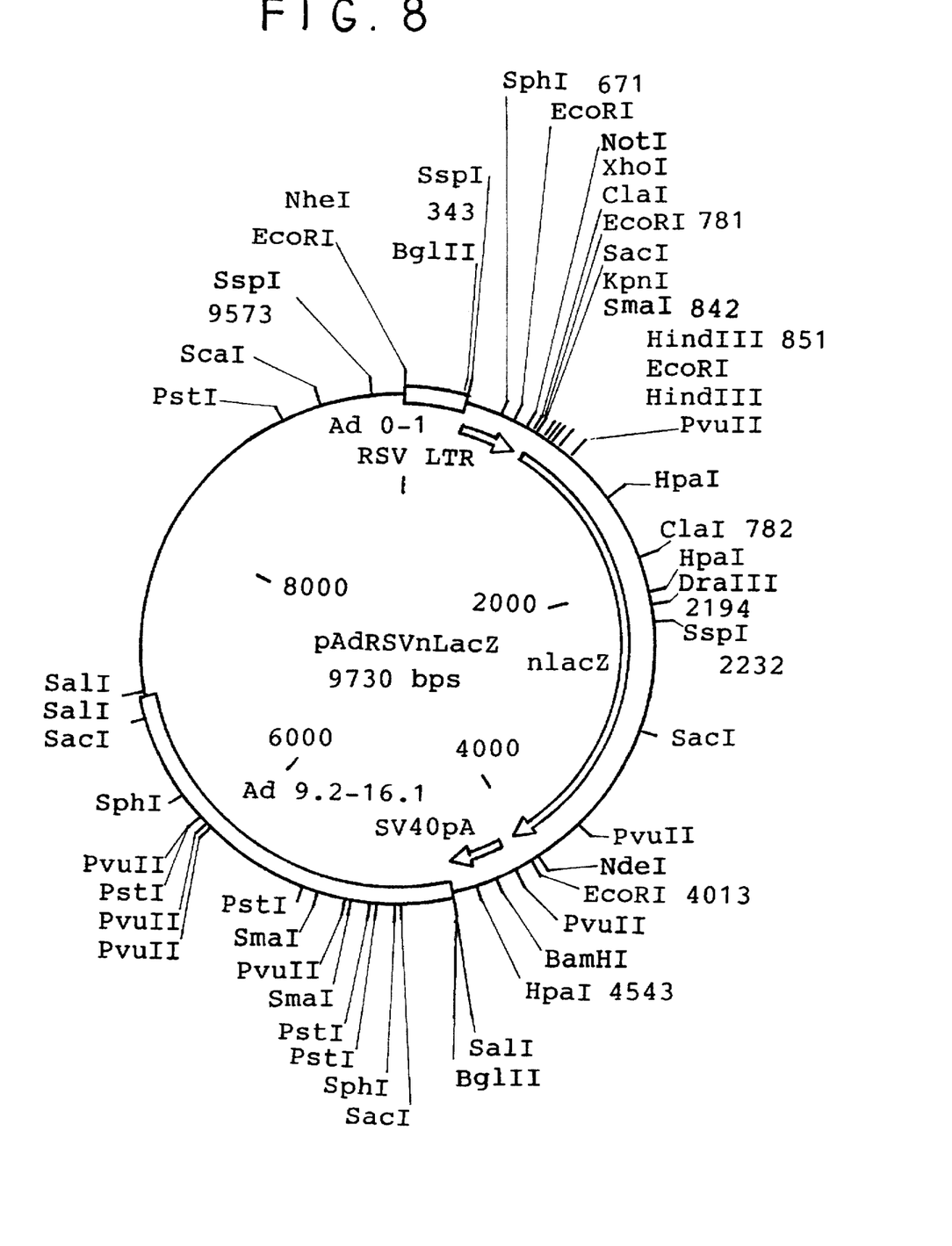
FIG. 8 is a map of plasmid pAdRSVnLacZ.

A second plasmid which provided the RSV-LTR promoter and nuclear targeting sequence for the lacZ gene was constructed as follows. The BgIII/XbaI fragment containing the nlacZ gene from plasmid LZ11 (Galileo, et al., *Proc. Natl. Acad. Sci.*, Vol. 87, pgs. 458–462 (1990)) (FIG. 4) was cloned into the blunted SmaI and BamHI sites of pSP72 (Promega) (FIG. 5) to form pSP72nLacZ (FIG. 6). From pSP72nlacZ, the BgIII/BamHI fragment containing the nlacZ gene was removed and cloned into the BamHI site of adRSV4 (FIG. 7) which was obtained from Dr. Beverly Davidson of the University of Michigan. The resulting plasmid is referred to as pAdRSVnLacZ (FIG. 8).

Figure 9:
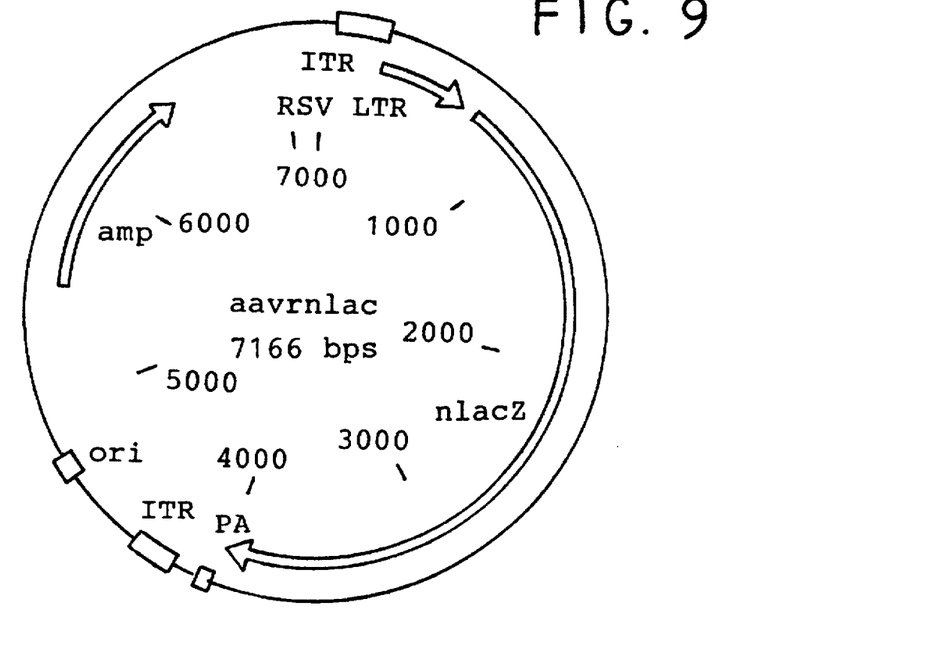
FIG. 9 is a map of plasmid AAVrnLac.

AAVrnLac (FIG. 9, ATCC No. 69492) was produced by inserting the SspI/DraIII fragment from pAdRSVnLacZ which contained the RSV-LTR promoter, nuclear targeting signal linked to the lacZ gene into the PmlI/DraIII site of TRF169.

B. Construction of SV40 oriAAV

Figure 10:
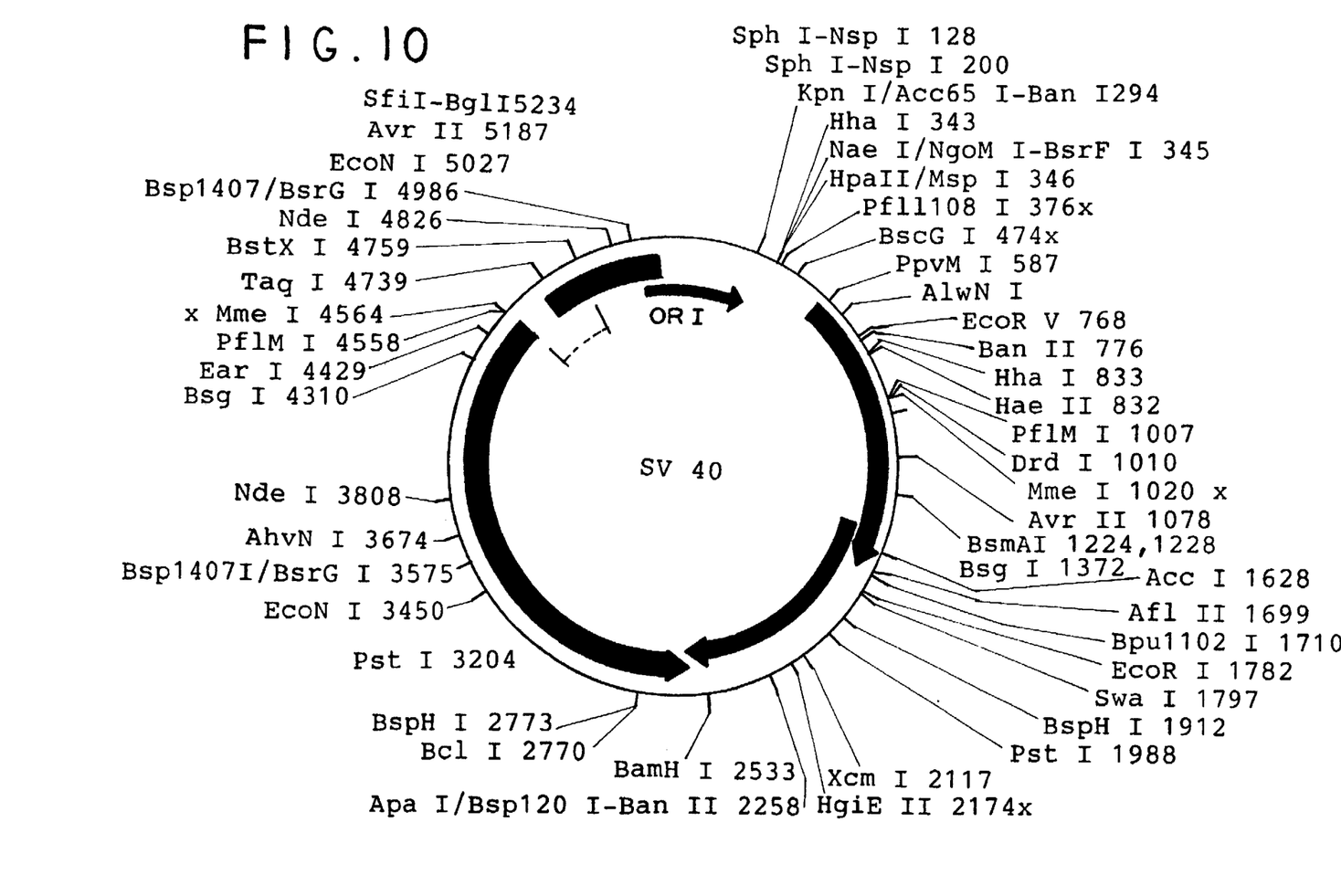
FIG. 10 is a map of SV40.
Figure 11:
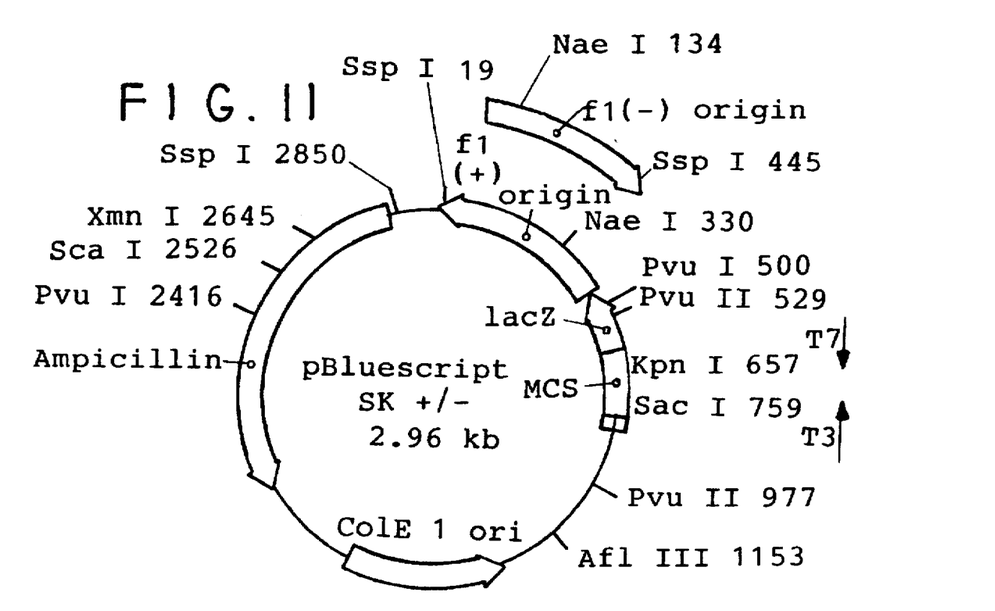
FIG. 11 is a map of plasmid pBluescriptSK.
Figure 12:
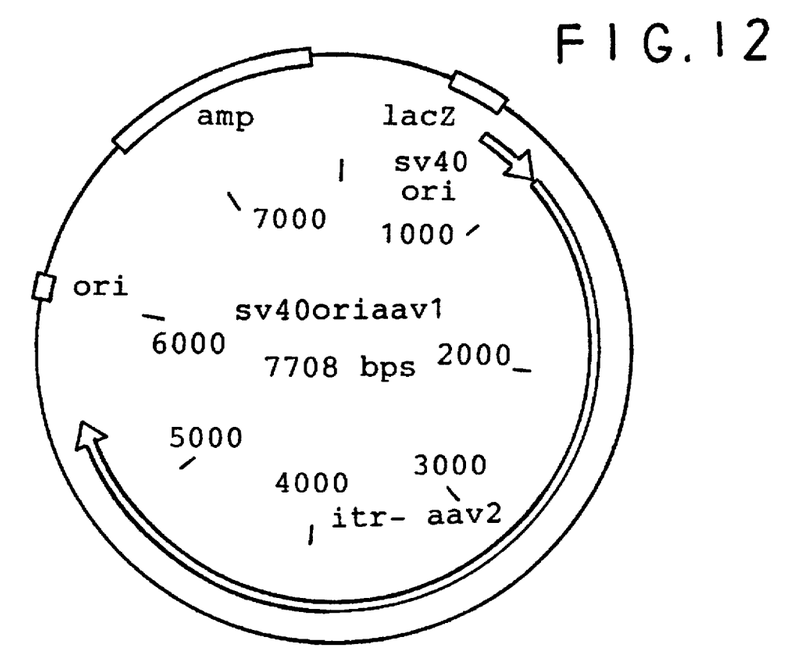
FIG. 12 is a map of plasmid pSV40 ori AAV1.

The SV40 origin of replication was removed from SV40 viral DNA (FIG. 10) by digestion with AvrII and PvuII. The fragment was blunted and cloned into the EcoRV site of pBluescript sk$^+$. (FIG. 11) (Stratagene.) The BalI fragment from pAV2 which contains the rep and cap genes was cloned into the SmaI site of the above vector to form SV40oriAAV. (FIG. 12).

Figure 13:
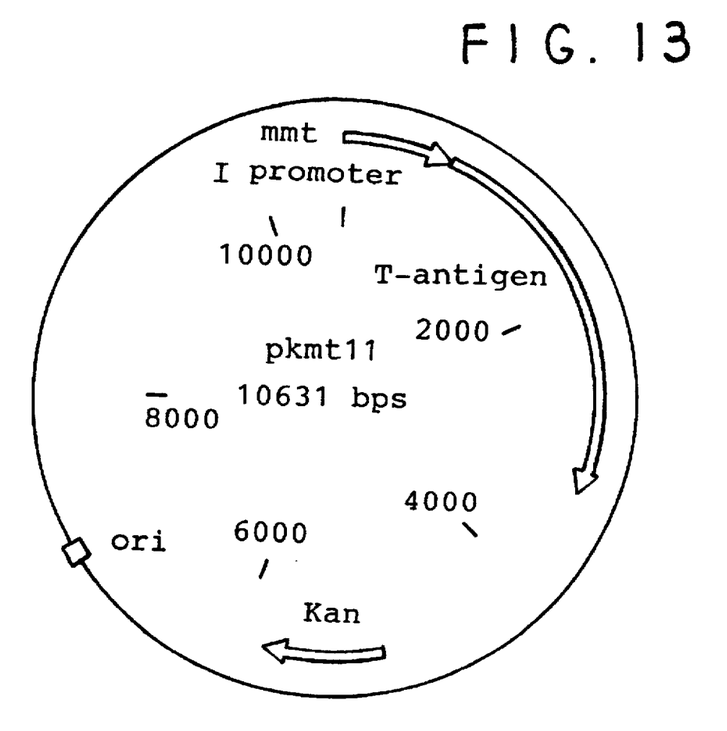
FIG. 13 is a map of plasmid pKMT11.

C. Production of Recombinant Virus pKMT11 (FIG. 13) was constructed as described in Gerard, et al., *Molecular and Cellular Biology*, Vol. 5, No. 11, pgs. 3231–3240 (Nov. 1985). pKMT11 then was transfected into CV-1 monkey cells to generate the CMT3 cell line. (Gerard, et al., 1985).

Eighteen to 24 hours prior to transfection, $2-5\times10^5$ CMT3 cells grown in D10 medium (DMEM (Bio Fluids) plus 10% fetal calf serum and 1× glutamine) are plated on a 10 cm dish. For transfection, 13.85 µg of an equal mixture of AAVrnLac and SV40oriAAv are combined with 25 µl of 10× Hepes Buffered Saline (HBS) and brought up to 250 µl with water. Separately, 70 µl of DOTAP, a cationic lipid (Boehringer Mannheim) is removed using a needle and syringe and added to 25 µl HBS and brought to final volume of 250 µl with water. The two tubes are combined and incubated for 10 mins. at room temperature. After the incubation period the media on the plates is removed, the cells rinsed with DMEM, and replaced with from 4 to 8 ml of DMEM. The DNA/DOTAP mixture then is added to the cells in a dropwise manner and the plates gently swirled to mix the contents. The plates then are returned to the incubator. After 6 hours, 4 to 8 ml of D10 medium supplemented with 200 µM ZnCl$_2$, 2 µM CdCl$_2$, and additional 10% fetal calf serum are added to the plates. The plates then are returned to the incubator for an additional 24 to 36 hours after which the medium is removed, the plates washed with DMEM, and $8\times10^6$pfu of Adenovirus 5 in 1.5 ml DMEM then is added. The plates are returned to the incubator and gently agitated every 15 minutes of one hour. After 1 hour, 8 ml of complete D10 medium are added to the plates and the infection is allowed to progress for 60 hours. The cells then are scraped gently from the plate and transferred to a 50 ml conical tube. The plates are rinsed with phosphate buffered saline (PBS), which also is transferred to the conical tube and centrifuged at 1,500 xg for 5 minutes. The supernatant is removed, the pellet is resuspended in PBS, and the centrifugation is repeated. The pellet then is resuspended in 1 ml of PBS, and the cells are lysed by three rounds of freezing in a dry ice ethanol bath for 5 minutes and then heating to 37° C. in a water bath for 5 minutes.

The concentration of recombinant AAV produced in the vector preparation was determined by a DNA slot-blot hybridization technique similar to that described by Samulski, et al, (*J. Virology*, Vol. 63, pgs. 3822–3828 (1989). Briefly, 55 ul of the cleared viral lysate supplemented with 5.5 ul of React 2 buffer (BRL) was digested for 30 min. at 37° C. with 3 units of DNAse 1 (Promega). This amount of DNAse 1 was sufficient to digest completely a control reaction containing 2 ug of ΦX174 Hae III digested DNA (BRL). After digestion the reaction was stopped by the addition of EDTA to a final concentration of 20 mM. This procedure eliminates any recombinant DNA not packaged into viral particles from the lysate. The viral lysate was then serially diluted and 1/10 volume of 3N NaOH was added to each dilutation then incubated at 65° C. for 1 hr. This procedure releases and denatures the recombinant AAV DNA from the assembled AAV viral particles. Next an equal volume of 2M NH₄OAc (pH 7) was added to the dilutions to neutralize the base. The samples were then applied to a Nytran membrane (Scheleicher and Schuell) using a vacuum blotter (BRL). The bound material was cross linked to the membrance using a Photodyne cross linker for 2 min. For purposes of quantitation, a serial dilution of the vector plasmid was made and applied to the filter. This series was treated the same as the viral preparation samples except the initial DNAse 1 digestion step was omitted. The blot then was prehybridized in Hyb buffer (0.5M sodium phosphate (pH 7), 7% SDS, 1% BSA, 1 mM EDTA) for 1 hr at 65° C., then hybridized overnight with a radiolabeled fragment isolated from the β-gal gene contained in the vector. The probe was radiolabeled using a random priming kit (BRL) with α-$^{32}$PdCTP (3000 ci/mMol Amersham). After hybridization the blot was washed three times at 65° C. The labeled blot was then exposed to X-ray film and the intensity of the dots from the serial dilution of the viral preparation were compared to the standard curve provided by the vector plasmid. A factor of two was used to correct for the plasmid vector being double stranded DNA and the virus existing as single stranded DNA. Using this procedure, a viral concentration of 1×10$^{10}$ viral genomes/ml of cell lysate was obtained.

The biological titer of the recombinant virus preparation was determined by transducing 293 cells with a serial dilution of the viral preparation. The number of blue colonies, which reflects the expression of β-galactosidase activity, were then counted. Briefly, 5×10$^4$ 293 cells grown in I10 media (IMEM, 10% fetal calf serum, 1× glutamine) were plated in a 6 well dish 24 hrs. prior to infection. The cells were infected by first rinsing the wells twice with IMEM media and then adding a serial dilution of the virus to the cells in a total of 150 ul. The cells were then returned to the incubator and gently agitated every 10 min for 1 hr. After this period of time 3 ml of I10 media was added back to the cells and they were allowed to grow for 48–60 hrs. Next the media was removed, the cells rinsed with 1× PBS and incubated with 2% formaldehyde and 0.2% glutaraldehyde for 5 min. The wells were then rinsed twice with 1× PBS and 2 mls of warmed staining reagent (5 mM potassium ferricyanide, 5 mM potassium ferrocyanide, 2 mM magnesium chloride in 1× PBS with a 1:40 dilution of 40 mg/ml X-gal in DMSO added just prior to straining) was added. The plates were then placed at 37° C. for 2–15 hrs. The number of blue cells were counted and used to determine the biological titer of the virus. As a control, a well of uninfected cells was present on the plate and used to monitor endogenous B-gal staining.

It is to be understood, however, that the scope of the present invention is not to be limited to the specific embodiments described above. The invention may be practiced other than as particularly described and still be within the scope of the accompanying claims.

What is claimed:

1. A vector system for enhanced production of infectious adeno-associated virus particles comprising:
    a first vector, said first vector being an adeno-associated viral vector, said first vector including, in a 5' to 3' direction, an adeno-associated virus 5' ITR; at least one heterologous DNA sequence; and an adeno-associated virus 3' ITR; and
    a second vector including an inducible origin of replication selected from the group consisting of an SV40 origin of replication, and a polyoma origin of replication, said inducible origin of replication capable of being activated by an agent, and said second vector also containing a DNA sequence encoding the adeno associated virus rep protein, and a DNA sequence encoding the adeno-associated virus cap protein, said second vector being free of adenoviral DNA sequences.

2. The vector system of claim 1 and further comprising a third vector including a DNA sequence encoding said agent and an inducible promoter controlling expression of said DNA sequence encoding said agent.

3. The vector system of claim 2 wherein said inducible origin of replication is the SV40 origin of replication, said agent is the SV40 T-antigen, and said inducible promoter is a metallothionein promoter.

4. Packaging cells transfected with the vector system of claim 1.

5. A vector system for enhanced production of infectious adeno-associated virus particles comprising:

a first vector, said vector being an adeno-associated viral vector, said vector including, in a 5' to 3' direction, an adeno-associated virus 5' ITR, and at least one heterologous DNA sequence, and an adeno-associated virus 3' ITR;

a second vector including an SV40 origin of replication, said SV40 origin of replication capable of being activated by the SV40 T-antigen, and a DNA sequence encoding the adeno-associated virus rep protein, and a DNA sequence encoding the adeno-associated virus cap protein; and a third vector including a DNA sequence encoding the SV40 T-antigen, and the metallothionein protein promoter controlling expression of said DNA sequence encoding said SV40 T-antigen.

6. A vector system for enhanced production of infectious adeno-associated virus particles comprising:

a first vector, said first vector being an adeno-associated viral vector, said first vector including, in a 5' to 3' direction, an adeno-associated virus 5' ITR, at least one heterologous DNA sequence, and an adeno-associated virus 3' ITR; and a second vector including an SV40 origin of replication, said SV40 origin of replication capable of being activated by the SV40 T-antigen, and said second vector also containing a DNA sequence encoding the adeno-associated virus rep protein and a DNA sequence encoding the adeno-associated virus cap protein, said second vector being free of adenoviral DNA sequences.

\* \* \* \* \*

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 135 bases
        ( B ) TYPE: nucleic acid
        ( C ) STRANDEDNESS: single
        ( D ) TOPOLOGY: linear     ( i i ) MOLECULE TYPE: plasmid DNA     ( i x ) FEATURE:
        ( A ) NAME/KEY: multiple cloning site     ( x i ) SEQUENCE DESCRIPTION: SEQ ID NO: 1:

```
ATTTAGGTGA  CACTATAGAA  CTCGAGCAGC  TGAAGCTTGC  ATGCCTGCAG  GTCGACTCTA      60

GAGGATCCCC  GGGTACCGAG  CTCGAATTCA  TCGATGATAT  CAGATCTGCC  GGTCTCCCTA     120

TAGTGAGTCG  TATTA                                                         135
```